United States Patent
Buckland et al.

(10) Patent No.: US 6,727,219 B2
(45) Date of Patent: Apr. 27, 2004

(54) SINGLE DOSAGE OXIDIZING TREATMENT

(75) Inventors: Raymond Buckland, Ontario (CA); Martin Bartholomew Rybiak, Calgary (CA); Thomas Peter Tufano, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 105 days.

(21) Appl. No.: 10/188,170

(22) Filed: Jul. 1, 2002

(65) Prior Publication Data

US 2004/0002433 A1 Jan. 1, 2004

(51) Int. Cl.[7] .......................... C11D 17/00; C11D 3/00; C11D 3/48
(52) U.S. Cl. .................. 510/439; 510/367; 510/382
(58) Field of Search ................. 510/367, 382, 510/439

(56) References Cited

U.S. PATENT DOCUMENTS

| 3,580,390 A | 5/1971 | Shull |
| 3,634,260 A | 1/1972 | Pickin |
| 4,973,416 A | 11/1990 | Kennedy |
| 6,228,825 B1 | 5/2001 | Gorlin et al. |

FOREIGN PATENT DOCUMENTS

| CA | 2039001 | 9/1991 |
| CA | 2314363 | 1/2001 |
| CA | 2323780 | 4/2001 |
| DE | 199 61 661 A | 12/2000 |
| EP | 387 165 A | 9/1990 |
| GB | 2 024 193 A | 1/1980 |
| JP | 93214398 A | 8/1993 |
| JP | 10-59803 A | 3/1998 |
| JP | 2814142 B | 10/1998 |
| JP | 1999171131 A | 6/1999 |
| JP | 1999246317 A | 9/1999 |

OTHER PUBLICATIONS

McQuillan, Blair, *On The Market*, Pool & Spa Marketing, Spring 2002, , p. 14.

*Primary Examiner*—Mark Kopec
*Assistant Examiner*—John M. Petruncio

(57) ABSTRACT

An oxidizing agent comprising a pre-measured amount of stabilized potassium hydrogen peroxymonosulfate in a water-soluble sealed pouch, said agent and pouch together having a specific gravity exceeding about 1.0, and a method for use of the oxidizing agent are disclosed.

18 Claims, No Drawings

SINGLE DOSAGE OXIDIZING TREATMENT

BACKGROUND OF THE INVENTION

Packaged, pre-measured, single-dose quantities of chemical reagents for use as laundry bleaching agents, solid and liquid laundry detergents, nonaqueous dishwashing formulations, and pigmentation formulations are known. For example, Gorlin et al. in U.S. Pat. No. 6,228,825 disclose a liquid automatic dishwashing cleaning formulation, optionally containing up to 20% of an oxygen bleaching agent, including potassium monopersulfate. Pesticides and soil treatment formulations for single-dose application have been similarly disclosed.

A major advantage of the use of such packaged single-dose application units is that the end user is provided a pre-measured amount of reagent, and avoids the hazards associated with direct contact with solid and liquid formulations (e.g., dust inhalation, skin or eye contact irritation). Thus problems common to the use of liquid and solid formulations such as waste through excessive use, inadequate treatment, and health hazards due to exposure are simultaneously minimized.

A need exists for single dose units for moisture sensitive materials wherein it is desired for the packaging to be dissolved in water. It is desirable to have moisture sensitive materials in pre-measured single-dose packages for oxidizing agents for pools, spas, and other ornamental or recreational water. The present invention overcomes the moisture sensitive problem and provides such a pre-measured oxidizing agent.

SUMMARY OF THE INVENTION

The present invention comprises an oxidizing agent comprising a pre-measured amount of stabilized potassium hydrogen peroxymonosulfate in a sealed water-soluble pouch, said agent and pouch together having a specific gravity exceeding 1.0.

The present invention further comprises a method of treating water comprising adding to the water a sealed water-soluble pouch containing a pre-measured amount of an oxidizing agent comprising stabilized potassium hydrogen peroxymonosulfate, wherein said agent and pouch together have a specific gravity exceeding 1.0.

DETAILED DESCRIPTION

Potassium hydrogen peroxymonosulfate ($KHSO_5$) is known to be chemically unstable in that the oxygen will readily react. It is therefore typically used in the form of a salt which is more stable. The term "stabilized potassium hydrogen peroxymonosulfate" is used herein to denote potassium hydrogen peroxymonosulfate and stabilized compositions thereof. This includes salts of potassium hydrogen peroxymonosulfate. In particular it includes the mixed triple salt $2 KHSO_5 \cdot KHSO_4 \cdot K_2SO_4$, a crystalline salt of enhanced stability having a theoretical active oxygen content of 5.2%, and commercial versions thereof typically having an active oxygen content of 4.7%. Stabilized potassium hydrogen peroxymonosulfate is used as an auxiliary oxidant or water shock treatment for pools, spas, and other recreational and ornamental waters, including for example fountains, reflecting pools, ornamental ponds, and the like. It is used to reduce the non-microbial waste content and restore the sparkle and clarity of such bodies of water and to do so without forming the irritating and malodorous chloramines associated with chlorinating products such as calcium hypochlorite.

Stabilized potassium hydrogen peroxymonosulfate is not a registered sanitizer and is used in conjunction with EPA-registered sanitizers. Stabilized potassium hydrogen peroxymonosulfate, in contrast to chlorine bleaches such as calcium hypochlorite, provides oxidation without undesirable side-effects such as bleaching or fading of vinyl liners, painted surfaces, or swimsuit fabrics.

Stabilized potassium hydrogen peroxymonosulfate in the form of the triple salt is available commercially as the active ingredient in OXONE monopersulfate compound available from E. I. Du Pont de Nemours and Company, Wilmington Del. Trademarks are hereinafter shown in upper case. OXONE is a stable, solid, water-soluble, non-chlorine-containing oxidizing agent with uses in swimming pool and spa oxidation products.

Other uses include the active bleach component in denture cleansers and other cleaning compositions, a microetchant in printed circuit board manufacture, a paper repulping aid for the destruction of wet strength resins, and an oxidizer in antimicrobial compositions.

OXONE is moisture sensitive but is known to be compatible in blends with anhydrous ingredients, such as anhydrous sodium carbonate, and with chemicals in which bound water is held tightly. For instance, blends with anhydrous sodium perborate and the monohydrate are stable, but blends with sodium perborate tetrahydrate are not. OXONE is shipped in drums and containers that have moisture barrier properties built into the packaging. This sensitivity to moisture has prevented stable packaging in water-soluble films that contain significant levels of moisture to provide the characteristic soft and "skin-like" feel of the plastic.

Stabilized potassium hydrogen peroxymonosulfate is typically used as a freshly-prepared solution, or, for such uses as swimming pools, is often "broadcast" directly from the bulk container in its original granular form onto the water surface using a scoop or shovel. Careless application of stabilized potassium hydrogen peroxymonosulfate can lead to overdosage, underdosage, and exposure to dust.

The present invention is directed to a pre-measured single use dose for stabilized potassium hydrogen peroxymonosulfate as an oxidizing agent for water treatment. It comprises a pre-measured amount of stabilized potassium hydrogen peroxymonosulfate as the oxidizing agent, in a sealed pouch, wherein said agent and pouch have a specific gravity exceeding 1.0. This invention simultaneously provides sufficient moisture protection for the stabilized potassium hydrogen peroxymonosulfate, immediate sinking of the product to the bottom of the body of water being treated, and rapid disintegration of the packaging in ambient temperature water. The contents of the pouch are thus fully released and dissolved and become uniformly distributed by the water movement associated with the circulation system.

Any grade of stabilized potassium hydrogen peroxymonosulfate is suitable for use in the present invention. Typically, the stabilized potassium hydrogen peroxymonosulfate is a free-flowing fine granular solid, having a particle size range of from about 45 to about 1200 micrometers. Preferred is OXON® or the stable triple salt form of stabilized potassium hydrogen peroxymonosulfate. Preferably it is used in the form of a dry solid having a maximum moisture content of less than 0.1%, measured by weight loss on heating at 65° C. for 30 minutes, and has a bulk density of from about 72 to about 81 lb/ft$^3$ (1.15–1.30 g/cm$^3$).

The stabilized potassium hydrogen peroxymonosulfate is optionally blended with other water treatment chemicals. The types of optional additives are given below as examples and are not intended to be all-inclusive. Examples are pH buffers to help maintain correct pH and alkalinity (e.g., anhydrous carbonates such as sodium carbonate, sesquicarbonates, bicarbonates such as sodium bicarbonate, silicates, bisulfates, and phosphates such as monopotassium phosphate and dipotassium phosphate); diluents, (e.g., sodium sulfate); clarifiers (e.g., anionic, nonionic, and cationic polymers, chitin and chitosan, aluminum and iron salts such as sulfates); algae control agents (e.g., copper salts such as sulfate, metal ions such as silver and zinc, quaternary ammonium chloride products such as alkyl dimethyl benzyl ammonium chloride formulations, and polymeric quaternary ammonium chloride products); active halogens and halide salts (e.g., trichloro-s-triazine trione, sodium dichloro-s-triazine trione, halogenated hydantoins such as 3-bromo-1-chloro-5,5-dimethylhydantoin, sodium chloride, sodium bromide, oxazolidinone compounds such as 3-halo-5-halomethyl-2-oxazolidinone); other oxidizers (e.g., persulfates such as sodium peroxydisulfate, other peracids, percarbonates); halogen stabilizers (e.g., cyanuric acid, sulfamic acid, and dimethylhydantoin); biocidal polymers such as poly(hexamethylenebiguanide); miscellaneous water modifiers (e.g., calcium chloride, chelating agents such as ethylenediamine tetraacetic acid, diethylenetriamine pentaacetic acid, and citric acid); corrosion inhibitors; fluorosurfactants; enzymes; lanthanum salts such as the carbonate and chloride; activators such as tetraacetylethylenediamine and ketones; surfactants; fragrances; dyes; and colorants.

As a swimming pool and spa oxidative treatment, the amount of stabilized potassium hydrogen peroxymonosulfate used is determined by the volume of water to be treated and the extent of contamination (so-called "bather load"). Typical recommended stabilized potassium hydrogen peroxymonosulfate usage rates are from about 1 to about 2 oz./250 gal (0.03–0.06 kg/m$^3$) for spas and about 1 lb/10,000 gal (0.012 kg/m$^3$) for swimming pools. Usage rates for other uses are as recommended by the manufacturers and distributors.

Thus, convenient pouch contents range from about 1 oz to about 10 lb., (30 g to 5 kg), and preferably from about 1 oz. to about 1 lb. (30 g to 500 g) for spa and pool use. In practice, for larger pools several smaller pouches are preferable to one 5 kg pouch, since the smaller pouches are both easier to handle and can be used to provide a better distribution of the stabilized potassium hydrogen peroxymonosulfate in the pool. Pouches of stabilized potassium hydrogen peroxymonosulfate for other uses would include amounts as small as 1 g.

Any water-soluble packaging resin compatible with the stabilized potassium hydrogen peroxymonosulfate is suitable for use to form the pouch in the present invention. Preferred is packaging resin in the form of a film. Examples of suitable water-soluble films include poly(vinyl alcohol), quaternized protein hydrolyzates, quaternized polyamines, polyvinylpyrrolidone, acrylic acid-maleic acid copolymers, polyphosphates, and dextrin derivatives.

The preferred water-soluble film is poly(vinyl alcohol), abbreviated herein as PVA, prepared by the hydrolysis of poly(vinyl acetate). PVA is commercially available with varying degrees of hydrolysis, and in a variety of grades, differentiating the product by various properties.

The packaging resin suitable for use herein is typically in the form of a film having a thickness of from about 0.001 to about 0.006 in (25 to 152 micrometers), preferably from about 0.0015 to about 0.003 in (38 to 76 micrometers). It has an equilibrium moisture content at 50% relative humidity and 23° C. of less than about 8.0%, preferable less than about 6.5%, and more preferably less than 6.0%. Stabilized potassium hydrogen peroxymonosulfate slowly degrades with the evolution of oxygen under conditions of high relative humidity, so the pouches are typically protected by storage in a secondary container. Such suitable secondary containers are, for instance, high-density polyethylene containers with tight-fitting closures. Prolonged storage of unprotected pouches in a high relative humidity environment, or packaging using a film grade with high equilibrium moisture content, are prone to cause the pouches to bloat and lose the desired ability to sink in water. Additional requirements for the film are the absence of additives subject to oxidation by stabilized potassium hydrogen peroxymonosulfate and maintenance of physical properties such as flexibility, strength, tear resistance, dissolution time in water, and physical appearance while in contact with the stabilized potassium hydrogen peroxymonosulfate. Additives that cause film gelling or crosslinking, such as borates in the case of PVA film, should be avoided as additives to the stabilized potassium hydrogen peroxymonosulfate.

Preferred packaging films are PVA resins containing small quantities of inert fillers to provide increased film-to-film slip (or lower tack) for ease of handling and reduced risk of tearing. Suitable fillers or extenders are well known to those skilled in the art, are used in amounts that do not diminish water sparkle when the film dissolves in water, and include alumina, calcium carbonate, silica, starch, dextrin, and clays.

Chemicals, such as borax, that tend to gel or cross-link PVA resins should be avoided, as they will interfere with the dissolution of the packaging material. Many PVA resins also contain water-soluble organic plasticizers, such as hydroxyl compounds. The most widely used such plasticizer is glycerol.

Examples of films meeting all of these requirements are PVA MONOSOL M9500 and MONOSOL M7031. MONOSOL M7031 is preferred. MONOSOL PVA films are available from MonoSol, LLC, Portage, Ind.

Although both the film and the pouch contents have densities greater than 1 g/cm$^3$, air can be trapped in the sealed pouch during the packaging process. Unless this air is removed during the sealing process to collapse the film against the contents, the pouches tend to float when placed in the body of water to be treated. Unless the pouch sinks, a partially immersed film dissolves in a non-uniform manner and the floating pouches are esthetically displeasing. Sufficient removal of air is required such that the specific gravity of the sealed pouch together with its contents, exceeds 1.0, and the pouch thus immediately sinks when placed in the body of water. Preferably the specific gravity of the sealed pouch, including its contents, is from about 1.0 to about 1.25, more preferably from about 1.05 to about 1.20.

Any convenient method for charging the stabilized potassium hydrogen peroxymonosulfate into the pouch, compressing the pouch to expel air, and sealing the pouch is suitable for use in the present invention. The pouches are sealed after expelling air from the package.

Sealing is typically accomplished by heat, using the film manufacturer's recommendations. Typically a pressure of from about 6 to about 7 bar (600 to 700 kPa), at a temperature of from about 160 to about 180° C., and a dwell time of about 0.3 to about 0.5 seconds is used. For higher volume commercial production, any suitable commercial packing equipment having the ability to compress the pouch prior to sealing (to remove sufficient air) is used. An example of a typical commercial volume filling line packages stabilized potassium hydrogen peroxymonosulfate (such as OXONE monopersulfate crystals from E. I. du Pont de Nemours and Company, Wilmington, Del.) in MONOSOL M7031 polyvinyl alcohol film [from MonoSol LLC, Portage, Ind.]. An Elpack Corporation GR-10M unit dosing mechanism [Even-Yehuda, Tel Aviv, Israel] is used in combination with a Hayssen Ultima 12-16 film package forming mechanism [Duncan, S.C.]. The stabilized potassium hydrogen peroxymonosulfate is introduced to the unit dosing mechanism from a flexible bulk intermediate container via a feed hopper. The unit dosing mechanism delivers a pre-measured dose to the forming collar of the form-fill-seal machine in response to a signal sent from the form-fill-seal machine control logic. The dose is sealed into a pouch of film according to normal machine operation, and is delivered to a packaging table or container via an inclined conveyor. Packaged doses are placed in suitable containers for shipment. The manufacturers' recommendations for operating this equipment are followed.

The equipment listed above is an example of equipment suitable for use in the present invention. Other suitable alternative equipment for these production steps can be employed. For instance, alternative weighers are combination weighers as manufactured by Ishida Scales Mfg. Co., Ltd. (Kyoto, Japan) and linear net weighers as are manufactured by Optima Machinery Corp. (Schwabisch Hall, Germany), Parsons Scales, LLC (De Pere, Wis.), and Mettler (Toledo, Ohio). Other examples of form, fill, and seal machines are produced by Robert Bosch Corp., Packaging Machine Division (South Plainfield, N.J.), Rovema Packaging Machines L.P. (Lawrenceville, Ga.). Multi-lane form, fill, and seal machines are produced by Fres-co Systems USA, Inc. (Telford, Pa.) and Circle Packaging Machinery Co. (Green Bay Wis.).

In other embodiments of the present invention, stabilized potassium hydrogen peroxymonosulfate is packaged in quantities from 1 g to 5 kg for other uses such as the active bleach component in denture cleansers and other cleaning compositions, as a paper repulping aid for the destruction of wet strength resins, and as an oxidizer in antimicrobial compositions.

The present invention further comprises a method of treating water comprising adding to the water a sealed water-soluble pouch containing a pre-measured amount of an oxidizing agent comprising stabilized potassium hydrogen peroxymonosulfate, wherein said agent and pouch have a specific gravity exceeding 1.0. The oxidizing agent and pouch are as previously described above. One or more pouches are added to the water, preferably while any circulation system present is in operation. The amount of stabilized potassium hydrogen peroxymonosulfate used is determined by the volume of water to be treated and the level of contamination. Typical recommended stabilized potassium hydrogen peroxymonosulfate usage rates are from about 1 to about 2 oz./250 gal (0.03 to 0.06 kg/m$^3$) for spas and about 1 lb/10,000 gal (0.012 kg/m$^3$) for swimming pools. Usage rates for other uses are as recommended by the manufacturers and distributors. The method of the present invention is suitable for use in pools, spas, fountains, ponds, reflecting pools, and other recreational or ornamental waters.

The oxidizing agent and method of the present invention provide the advantage of single-dose application units. The end user is provided a pre-measured amount of reagent, and avoids the hazards associated with direct contact with the agent (e.g., dust inhalation, skin or eye contact irritation). Further advantages are the elimination of waste through excessive use of agent and inadequate treatment due to use of less agent than needed. Spills which result in wasted agent are less likely.

Test Methods

Detailed test methods for determining the compatibility of packaged chemicals with PVA and the solubility of PVA are available from MonoSol, LLC (1701 County Line Road, Portage, Ind. 46368). Methods used to determine the turbidity and active oxygen of pool water were as described in Example 3 hereinafter.

MonoSol Method MSTM 177, "Standard Test Method for Determination of Product Compatibility with MONOSOL Water Soluble Film" describes methods for measuring percent moisture content, and Fourier transform infrared (FTIR) spectra after specified times of storage of the packaged product in a controlled environment. FTIR spectra and solubility tests (by MSTM 205, below) are made on unexposed PVA film, and packaged product pouches are stored in the following environments:

20° C.+/−2° C., 50% relative humidity +/−10% relative humidity

38° C.+/2° C., 80% relative humidity +/−5% relative humidity

380° C.+/−2° C., 10% relative humidity +/−10% relative humidity

−20° C. alternating with 38° C.+/−2° C., 80% relative humidity +/−5% relative humidity Sample packages are removed after 7, 14, 21, 28, and 35 days. FTIR spectra of the films are measured after exposure. Moisture content is calculated based on peak heights in the FTIR spectra. Visual discoloration of the film, changes in film flexibility, changes in the appearance of the contents (including any bloating of the packages) are observed.

MonoSol Method MSTM 205, "Standard Test Method for Solubility of MONOSOL Water Soluble Film when contained within a Plastic Holder" measures the time for a water-soluble film to disintegrate and dissolve in water. Samples of unexposed and exposed film, prepared as in MSTM 177 above, are placed in a 35 mm slide mount and immersed in water stirred in beakers at 10° C. The times for the film to disintegrate and for film fragments to dissolve completely are measured. For MONOSOL M7031 PVA film, 38 micrometers in thickness, disintegration and dissolution times at 10° C. are about 12 s and 30 s, respectively.

EXAMPLES

Example 1

Sample packages of an 80/20 wt % OXONE/anhydrous sodium carbonate blend (20 g) were packaged in MONOSOL M7031 PVA film using small scale sealing equipment, with most of the air being squeezed out before final sealing. Several such packages were closed inside high-density polyethylene screw cap jars, such that the jars were approximately half-full, and stored at room temperature for 21 days. The pouches were removed and examined for any changes in film flexibility, appearance, rupture resistance, dissolution properties in water, and any tendency for the pouch to inflate. This procedure was repeated using MONOSOL M9500 PVA film instead of M7031. The resulting observations are shown in Table 1. Both films tested satisfactory for compatibility with contents.

Comparative Example A

The procedure of Example 1 was repeated using MONOSOL M7061 PVA film instead of M7031. The resulting observations are shown in Table 1. This data illustrates that a film having a high moisture content at 50% relative humidity and 23° C. is not suitable for use in packaging a moisture sensitive agent such as OXONE.

TABLE 1

Compatibility and Solubility Tests for OXONE packaged in PVA

| Observation | M7031 Example 1 | M9500 Example 1 | M7061 Comparative Ex. A |
|---|---|---|---|
| Film Flexibility | No change | No change | No change |
| Film Discoloration | Some white spots | No change | No change |
| Pouch Inflation (1) | None | None | Some inflation |
| Rupture Resistance | Good | Good | Good |
| Disintegration in Water | Minimal hindrance | No change | Limited hindrance |
| Dissolution Time | Slight increase | Significant increase | Significant increase |
| IR Carbonyl (2) | No change | Slight change in intensity and position | Slight change in intensity and position |
| Moisture Content at 50% relative humidity/23° C. | 5.8% | 6.4% | 8.6% |
| Nominal Tensile Strength/Modulus | 422/162 kg/cm² | 415/141 kg/cm² | 359/90 kg/cm² |
| Conclusion | Satisfactory, preferred | Satisfactory | Unsatisfactory (inflation) |

(1) Failure of this performance factor can lead to packages that float or even rupture.
(2) PVA contains some residual poly(vinyl acetate), which contributes IR absorption due to the carbonyl groups.

Example 2

An 85/15 wt % blend of OXONE monopersulfate crystals/anhydrous sodium carbonate (from E. I. du Pont de Nemours & Company, Wilmington, Del.) was packaged in MONOSOL M7031 polyvinyl alcohol film. The film roll had an 8 inch (20.3 cm) web, 1.5 mil (0.038 mm) thickness, was 400 yards (366 m) long, and wound onto a 3 inch (7.6 cm) core. An Elpack GR-10M unit dosing mechanism was used in combination with a Hayssen Ultima 12-16 film package forming mechanism (Hayssen, Duncan S.C.), used in accordance with the manufacturers' instructions.

The OXONE was introduced to the unit dosing mechanism from a flexible bulk intermediate container via a feed hopper. The unit dosing mechanism delivered a pre-measured dose of 500 g to the forming collar of the form-fill-seal machine in response to a signal sent from the form-fill-seal machine control logic. The dose was sealed into a pouch of M7031 film according to normal machine operation, and was delivered to the packaging table via an inclined conveyor. Packaged doses of OXONE PS16 were packed into a plastic (polyethylene) pail, and the pail was sealed prior to shipment.

The OXONE packaged according to this procedure was tested for pool water quality maintenance, and performed in a satisfactory manner.

Example 3

In simulation of a pool application, a tote tank, equipped with a sand-filtered circulation system, was fully charged with "pool water" (1200 L, adjusted to 22–24° C.). The filtration rate was 2.4 L/s, the turnover period 8.3 min. "Pool water" was water adjusted 1) for alkalinity using sodium bicarbonate to the required alkalinity of 100–120 mg/L calcium carbonate, 2) for hardness using calcium chloride to 240–260 mg/L calcium carbonate, 3) for residual free available chlorine using sodium hypochlorite to a level of 2–4 mg/L residual free available chlorine (expressed as $Cl_2$), and finally 4) to a pH of 7.4–7.6 with aqueous 18% hydrochloric acid. To generate turbidity, the 1200 L of pool water was treated with (a) a solution of synthetic sebum oil (1 g, formulation in Table 2, below) in "Reagent Alcohol" (200 mL) and (b) a suspension of bandy black clay (1 g in 200 mL water). Reagent Alcohol is a commercial blend of methanol, ethanol, and isopropyl alcohols available from VWR International, Bridgeport, N.J., as Reagent Alcohol, VW3609-4. Bandy black clay is available from H. C. Spinks Co., Paris, Tenn. After 30 min circulation to mix, the turbidity was measured using a Hach Ratio Turbidimeter (Hach Corporation, Loveland, Colo., used according to manufacturer's instructions). OXONE (30 g) was added from a scoop ("broadcast"). After 10 min circulation, a 10-mL sample was removed and analyzed titimetrically for active oxygen, using Method #4500CI-S (ferrous ammonium sulfate) in "Standard Methods for the Examination of Water and Wastewater", $19^{th}$ Edition, American Public Health Association, Washington, D.C., 1995. After 40 min., the turbidity was remeasured as above. Results are shown in Table 3.

The tank was flushed thoroughly, refilled, conditioned as before, and the turbidity measured. The conditioned pool water was dosed with 30 g OXONE sealed in a pouch of MONOSOL M7031 PVA film, prepared according to the procedure of Example 1. The pouch sank immediately, disintegrated within 15 seconds and film and OXONE completely dissolved within 40 seconds. The water was circulated for 10 and 40 min. and analyzed as before. The results, shown in Table 3, demonstrated that the packaged unit dosage and loose powder systems provided equal active oxygen and turbidity reduction.

TABLE 2

Composition of Synthetic Sebum Soil.

| Component* | % by weight | Constituent | % by weight |
|---|---|---|---|
| Palmitic Acid | 10.0 | Olive Oil | 20.0 |
| Stearic Acid | 5.0 | Squalene | 5.0 |
| Coconut Oil | 15.0 | Cholesterol | 5.0 |
| Paraffin Wax, m.p. 54–56°C. | 10.0 | Synthetic Sperm Wax | 15.0 |
| Oleic Acid | 10.0 | Linoleic Acid | 5.0 |

*All components of synthetic sebum oil are from Aldrich, Milwaukee, WI, except "synthetic sperm wax", which is available as CRODAMOL SS from Croda, Inc., Parsippany NJ.

TABLE 3

Comparison of Granular and Packaged OXONE

| Measurement | Time | Granular OXONE (Control) | Packaged OXONE |
|---|---|---|---|
| Turbidity, Initial | * | 0.90 NTU | 0.70 NTU |
| Turbidity, Final | 40 min.** | 0.59 NTU | 0.41 NTU |
| Turbidity Reduction | — | 0.31 NTU, 34% | 0.29 NTU, 41% |
| Active Oxygen | 10 min.** | 1.15 ± 0.02 microg/g | 1.14 ± 0.02 microg/g |

*Initial turbidity measurement made after conditioning and mixing, before addition of OXONE.
**Time measured from moment of addition of OXONE.

What is claimed is:

1. An oxidizing agent comprising a pre-measured amount of stabilized potassium hydrogen peroxymonosulfate in a sealed water-soluble pouch, said agent and pouch together having a specific gravity exceeding 1.0.

2. The agent of claim 1 wherein the stabilized potassium hydrogen peroxymonosulfate is a free flowing granular solid.

3. The agent of claim 2 wherein the stabilized potassium hydrogen peroxymonosulfate has a particle size of from about 45 to about 1200 micrometers.

4. The agent of claim 3 wherein the amount of stabilized potassium hydrogen peroxymonosulfate is from about 1 g to about 5000 g.

5. The agent of claim 1 further comprising a pre-measured amount of an agent selected from the group consisting of a pH buffer, clarifier, algae control agent, halogen salt, halide salt, oxidizer, halogen stabilizer, biocidal polymer, water modifier, corrosion inhibitor, fluorosurfactant, enzyme, lanthanum salt, activator, surfactant, fragrance, dye and colorant.

6. The agent of claim 1 wherein the pouch has a film thickness of from about 0.001 inch (25 micrometers) to about 0.006 inch (150 micrometers).

7. The agent of claim 1 wherein the agent and pouch together have a specific gravity between 1.0 and about 1.25.

8. The agent of claim 1 wherein the pouch comprises poly(vinyl alcohol) compatible with the stabilized potassium hydrogen peroxymonosulfate.

9. The agent of claim 8 further comprising sodium carbonate.

10. A method of treating water comprising adding to the water a sealed water-soluble pouch containing a pre-measured amount of an oxidizing agent comprising stabilized potassium hydrogen peroxymonosulfate, wherein said agent and pouch together have a specific gravity exceeding 1.0.

11. The method of claim 10 wherein the stabilized potassium hydrogen peroxymonosulfate is a free flowing granular solid.

12. The method of claim 11 wherein the stabilized potassium hydrogen peroxymonosulfate has a particle size of from about 45 to about 1200 micrometers.

13. The method of claim 12 wherein the amount of stabilized potassium hydrogen peroxymonosulfate is from about 1 g to about 5000 g.

14. The method of claim 10 wherein the oxidizing agent further comprises a pre-measured amount of an agent selected from the group consisting of a pH buffer, clarifier, algae control agent, halogen salt, halide salt, oxidizer, halogen stabilizer, biocidal polymer, water modifier, corrosion inhibitor, fluorosurfactant, enzyme, lanthanum salt, activator, surfactant, fragrance, dye and colorant.

15. The method of claim 10 wherein the pouch has a film thickness of from about 0.0015 inch (38 micrometers) to about 0.003 inch (76 micrometers).

16. The method of claim 10 wherein the agent and pouch together have a specific gravity between 1.0 and about 1.25.

17. The method of claim 10 wherein the pouch comprises poly(vinyl alcohol) compatible with the stabilized potassium hydrogen peroxymonosulfate.

18. The method of claim 17 further comprising sodium carbonate.

* * * * *

UNITED STATES PATENT AND TRADEMARK OFFICE
CERTIFICATE OF CORRECTION

PATENT NO.     : 6,727,219 B2
DATED          : April 27, 2004
INVENTOR(S)    : Buckland Raymond, Rybiak Martin Bartholomew and Tufano Thomas P.

It is certified that error appears in the above-identified patent and that said Letters Patent is hereby corrected as shown below:

Column 9,
Line 4, after "water-soluble pouch," insert -- having a film equilibrium moisture content at 50% realtive humidity and 23°C of less than about 8.0%, --
Line 33, after "sealed water-soluble pouch" insert -- having a film equilibrium moisture content at 50% realtive humidity and 23°C of less than about 8.0%, and --

Signed and Sealed this

Second Day of November, 2004

JON W. DUDAS
*Director of the United States Patent and Trademark Office*